(12) United States Patent
George et al.

(10) Patent No.: US 7,247,323 B2
(45) Date of Patent: Jul. 24, 2007

(54) DELIVERY SYSTEM FOR APPETITE SUPPRESSANT

(75) Inventors: Liliana George, Centerport, NY (US); Craig Tadlock, Islip Terrace, NY (US); Raffi Balian, Bay Shore, NY (US); Monica Apostol, Coram, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 11/464,655

(22) Filed: Aug. 15, 2006

(65) Prior Publication Data

US 2007/0042058 A1 Feb. 22, 2007

Related U.S. Application Data

(60) Provisional application No. 60/708,995, filed on Aug. 17, 2005.

(51) Int. Cl.
*A01N 65/00* (2006.01)

(52) U.S. Cl. .................... 424/725; 424/776; 424/779

(58) Field of Classification Search .................... None
See application file for complete search history.

(56) References Cited

U.S. PATENT DOCUMENTS

| | | | |
|---|---|---|---|
| 2,177,679 A | 10/1939 | Weisbender | |
| 5,407,665 A | 4/1995 | McLaughlin et al. | |
| 5,869,063 A * | 2/1999 | Lezdey et al. | 424/401 |
| 6,376,657 B1 | 4/2002 | Van Heerden et al. | |
| 2002/0037303 A1* | 3/2002 | Deckers et al. | 424/401 |
| 2003/0095936 A1* | 5/2003 | Light | 424/64 |
| 2004/0071747 A1* | 4/2004 | Kume et al. | 424/401 |
| 2004/0096479 A1 | 5/2004 | Levine | |
| 2004/0156920 A1* | 8/2004 | Kane | 424/725 |
| 2004/0247702 A1* | 12/2004 | Rajendran et al. | 424/725 |

FOREIGN PATENT DOCUMENTS

| WO | WO 9818472 | 5/1998 |
|---|---|---|
| WO | WO01/03714 | 1/2001 |

OTHER PUBLICATIONS

Derwent-acc: 2001-112573, Jan. 2001, PCT, Green et al.*
Boozer CN, et al., "An Herbal Supp. Cont. Ma Huang-Guarana for weight loss: a random., dble-blind trial." Int J Obes Relat Metab Disord, Mar. 2001,V.25,No. 3,pp. 316-324.(Abst), 1 page.
Phytobase Nutritionals Inc., "*Caralluma fimbriata*" [online], 2004-2006 [Retrieved on Aug. 4, 2006]. Retrieved from <http://caralluma.com>, 6 pages.
"Lipid Nutrition Introd. a New Ingred" [online], 2005 [Retrieved on Aug. 4, 2006]. Retrieved from: <http:www.npicenter.com/anm/termplates/newsATemp.aspx?article=12651&zoneid=9.>, 2 pages.
"Health-marketplace.com, Guarana" [online], 2005 [Retrieved on Mar. 10, 2005]. Retrieved from: http://www.health-marketplace.com/Guarana.htm.>, 3 pages.
"Yerba Mate", [online], 2005 [Retrieved on Nov. 14, 2006]. Retrieved from: <http://www.viable-herbal.com/singles/herbs/s587.htm.>, 6 pages.
Phytopharm plc, "Hoodia Gordonii Fact File" [Retrieved on Oct. 18, 2006] Retrieved from:<http//:www.phytopharm.com/hoodia_faq.html.>, 3 pages.
FDA Consumer magazine, "Losing Weight Safely" [Retrieved on Oct. 18, 2006] Retrieved from:<http://www.fda.gov/fdac/features/196_wght.html.>, 6 pages.
Amazing Nature, "GUARANA(*Paullinia cupana*)" [Retrieved on Nov. 4, 2002] Retrieved from: <http://amazing-nature.com/info/1119.htm.>, 2 pages.
"Maxam Nutraceutics View Product, ANAVONE" [Retrieved on Oct. 18, 2006] [Retrieved from: <http://ssl.maxamlabs.com/MAXAM_ASP_ViewProduct_LongDescription.asp?ProductINDX=85.>, 2 pages.
"GUARANA: Physical Stimulating and Lipolysis Activating", Prod. Info. Sheet, International Sourcing, Inc., Greentech S.A., (May 1998 as supplied by Greentech S.A. on Nov. 13, 2006), 2 pages.

* cited by examiner

*Primary Examiner*—Michael Meller
*Assistant Examiner*—Qiuwen Mi
(74) *Attorney, Agent, or Firm*—Peter Giancana

(57) ABSTRACT

The invention relates to a topical delivery system suitable for application to the lips, comprising at least one naturally occurring oil, at least one naturally occurring wax, and at least one naturally occurring diet aid. The invention also relates to a method for controlling weight in an individual by applying such a composition to the lips.

3 Claims, No Drawings

DELIVERY SYSTEM FOR APPETITE SUPPRESSANT

This application claims priority/benefit of U.S. 60/708,995, filed Aug. 17, 2005.

FIELD OF THE INVENTION

The invention is in the field of delivery systems for active agents. More specifically, the invention is a topical delivery system for appetite suppressants.

BACKGROUND OF THE INVENTION

It is widely recognized that the stress of the modern fast-paced world can frequently lead to overeating, which in turn may lead to unhealthy physical characteristics, such high cholesterol, high blood pressure, heart disease, and diabetes etc. In many cases, the stress of weight gain may give rise to low self-esteem, resulting in further overeating, thereby initiating an endless cycle of poor eating habits.

The modification of eating patterns is of course desirable, but establishing good habits are difficult based on sheer will power. Diet aids can provide assistance, but it is often difficult for the user to remember to take numerous capsules or pills every day, and/or it may not always be convenient to take them at the time required. Thus, an improvement in the dieting process would be to have a mechanism of accessing diet aids that would be more automatic, almost passive, so as part of the user's daily routine it may provide a better opportunity for success rather than a rigid schedule of pill-taking. The present invention now provides a means by which a dieter may be able to incorporate one or more diet aids into an activity that is performed automatically each day, thereby potentially increasing the chances of compliance and success, by virtue of the passive intake of the diet aid.

SUMMARY OF THE INVENTION

The present invention relates to a topical composition suitable for application to the lips, comprising at least one naturally occurring oil, at least one naturally occurring structuring agent, and at least one naturally occurring diet aid. The topical composition suitable for application to the lips is in one embodiment a lipstick or in another embodiment is a lip gloss. In the lipstick or lip gloss of the present invention the structuring agent is wax; and they each comprise as the diet aid at least one of pine nut (Korean) seed oil, *caralluma fimbriata* stem extract, and guarana seed extract. The invention also provides a method for delivering a diet aid to an individual and for controlling the weight of the individual. The methods comprise applying to the lips of the individual a topically acceptable composition comprising at least one naturally occurring oil, at least one naturally occurring wax, and at least one naturally occurring diet aid.

DETAILED DESCRIPTION OF THE INVENTION

The present invention provides a convenient vehicle for delivering diet aids to an individual in a manner that coincides with the normal daily routine of the individual. In brief, one or more diet aids are incorporated into a vehicle adapted for topical application to the lips, for example, a lipstick, lip gloss or lip balm. The individual wishing to employ the diet aid applies, to his or her lips, the lip vehicle containing the diet aid in place of his/her usual lip product. It is common for users of lip products to lick or bite their lips routinely, thereby possibly ingesting some lip product throughout the day. The incorporation of the diet aid into a lip product therefore places the diet aid in a position where it may be routinely but passively ingested, if desired, thereby avoiding the need for the user to remember to take capsules or other inconvenient forms of administration.

One of the advantages of the present invention is that it relies partially or completely on the use of naturally occurring materials. The principle components of the lip product are one or more oils, one or more waxes or functionally similar structuring agents, and one or more diet aids themselves, each of which is a naturally occurring material. By "naturally occurring material", as used herein, it is meant the material that is found normally in nature, or is readily extracted or derived from a natural source, such as a plant, animal or mineral source. Also included in this definition are synthesized materials that are chemically substantially identical to naturally occurring materials, e.g., synthetic vanillin, or synthetic triglycerides that are the reaction products of glycerol and fatty acids, each of which occur in nature. Preferably, the delivery system of the invention contains at least 50% by weight of the composition naturally occurring components, more preferably at least 75% naturally occurring components, more preferably still at least 90% naturally occurring components, and most preferably substantially all naturally occurring components. All components employed in the delivery system should be selected from those considered to be safe for human ingestion, i.e., that are routinely used in food. The majority of the components are preferably food grade, and the majority of the components are more preferably GRAS (Generally Recognized as Safe). Components meriting such a designation are found in Title 21 of the US Code of Federal Regulations, Part 182, the contents of which are incorporated herein by reference. When the components are GRAS, it is particularly preferred that the compositions of the present invention comprise at least 50% by weight of the composition of GRAS components, more particularly preferably at least 75% GRAS components, and most particularly preferably, the composition will be substantially entirely GRAS components.

A substantial and key component of the lip delivery system is one or more oils. Oils that are useful in the delivery system of the present invention will be oils that are acceptable for cosmetic use on the lips and/or food use. The oils used in the delivery system may comprise any type of oil that is typically used in a product applied topically to the lips. Such oils include lanolin and lanolin derivatives, straight or branched chain volatile hydrocarbons having from 8-20 carbon atoms, such as decane, dodecane, tridecane, tetradecane, and C8-20 isoparaffins; nonvolatile hydrocarbons, such as isoparaffins, squalane, or petrolatum; esters having the formula RCO—OR' wherein RCO represents a carboxylic acid radical and OR' represents an alcohol residue, such as isodecyl neopentanoate, tridecyl octanoate, cetyl palmitate, cetyl octanoate, cetyl stearate, cetyl myristate, isopropyl palmitate, isopropyl myristate, polyglyceryl-2-isostearate, neopentyl glycol distearate, isodecyl oleate, decyl isostearate, diisopropyl sebacate, PEG-4 diheptanoate, dioctyl malate, and isohexyl neopentanoate; and fatty alcohols, such as, for example, lanolin alcohol or oleyl alcohol.

As previously noted, the oil employed is a naturally occurring oil, preferably a plant-derived oil. Examples of such oils are soybean oil, rapeseed oil, palm oil, cotton seed oil, apricot kernel oil, sunflower seed oil, castor seed oil, palm oil, palm kernel oil, coconut oil, grape seed oil, black mustard oil, poppyseed oil, karite butter oil, sweet almond oil, avocado oil, jojoba oil, lupine oil, groundnut oil, sesame oil, olive oil, black cumin seed oil, borage oil, evening primrose oil, kukui nut oil, macadamia nut oil, marula oil, calendula oil, hempseed oil, corn oil, cocoa oil, castor oil, linseed oil, annatto oil, wheat germ oil, safflower oil, walnut oil, rosehip oil, cranberry oil, tea tree oil, hazelnut oil, and rice bran oil.

Also useful as part of the oil component are polyglycerides, i.e., esters of glycerol and two or more fatty acids, for example, di-, tri-, penta-, hepta- and decaglycerides. Such materials are frequently obtained or derived from saturated or unsaturated vegetable oils and fats such as soybean, corn, sunflower, high erucic acid rapeseed, low erucic acid rapeseed, canola, crambe, meadowfoam, cottonseed, olive, safflower, sunflower, sesame seed, nasturtium seed, tiger seed, ricebran, wallflower, and mustard seed; nut fats and oils such as coconut oil, babassu kernel oil, palm kernel oil, palm oil, or peanut oil; or cocoa butter and cocoa butter substitutes such as shea butter or illipe butter. Polyglycerides can also be obtained or derived from animal sources, such as meat fats (tallow or lard) or milkfat or butterfat. However, plant-derived polyglycerides, or synthetic polyglycerides based on natural fatty acids and glycerol are particularly preferred for use in the delivery system of the invention. The oil component of the system are typically used in an amount of from about 20-90% by weight of the total composition.

A second key component of the lip delivery system is at least one structuring agent, preferably a wax, or wax-like material. For purposes of the present specification and claims, waxes will be understood to encompass traditional waxes, namely those plant, animal or mineral waxes containing primarily esters of higher fatty acids and alcohols, free higher acids and alcohols, and saturated hydrocarbons; examples of such traditional waxes include, but are not limited to, beeswax, synthetic wax, shellac wax, spermaceti, lanolin wax, ozokerite, bran wax, ceresin wax, paraffin, rice wax and jojoba wax. However, it also includes other non-traditional wax-like materials, including, but not limited to various fatty alcohols, fatty acids, fatty esters, polyethylenes, polyethylene glycols, and sterols as well as synthetic resinous products having a wax-like, i.e., hard, brittle, relatively non-greasy, texture, such as silicone waxes. In a preferred embodiment, however, the wax component comprises one or more naturally-derived waxes, and preferably plant-derived waxes, such as carnauba wax, bayberry wax, beeswax, montan wax, candelilla wax, China wax, flax wax, pine wax, cotton wax, jojoba wax, ouricury wax, lignite wax, rice bran wax, sugar cane wax, Japan wax or cork fiber wax. The amount of the structuring agent employed will depend on the desired ultimate product form, i.e., a softer delivery vehicle, such as a pasty lip gloss in a pot, will employ less of the structuring agent, and a solid stick form will utilize a higher level of the structuring agent. Generally speaking, the structuring agents will be employed in a range of about 2 to about 20% by weight of the composition, and may be added in any combination suitable to achieve the desired texture in the finished product.

An essential component of the delivery vehicle is the diet aid itself. As used in the context of the present invention, the term "diet aid" will be understood to encompass a variety of functional categories, the members of which are believed to assist the user in losing weight, or controlling weight or appetite by any number of different effects or activities. One or more diet aids of different performance categories may be employed in a delivery vehicle. Preferably as previously noted, the diet aid is a naturally occurring material. A plant-derived or herbal material (e.g., whole plant material, such as leaves, stems, roots or combinations, or extracts of whole plant or plant parts), or any one or more of the isolated active components of the plant-derived or herbal materials is particularly preferred. As used below, reference to any plant will be understood to include whole plant, plant parts, extracts or isolated active components of the referenced plant or herb.

There is a wide variety of materials that are known or used for assisting in weight loss or control, and in many cases, materials can have multiple useful effects or activities. For example, diet aids as employed in the present invention may include components that are diuretics or mild laxatives, energy boosters or stimulants, agents to increase metabolism, agents to prevent fat storage or burn fat (thermogenic agents or fat reducers), appetite suppressants, fragrant sympathetic nervous system-stimulants, relaxants, agents to reduce stress or other materials that contribute to a state of being more amenable to dieting by losing or controlling weight. A preferred combination of effects or activities is a fat reducer, an appetite suppressant, a diuretic, and an agent to increase metabolism. Examples of diuretics or mild laxatives include but are not limited to materials such as dandelion root, corn silk, uva ursi leaf, cleavers herb, red clover blossom, chickory root, parsley leaf, olive leaf, black currant (extract of cassis), or senna leaf. In another category are energy boosters or stimulants, such as caffeine, yerba mate leaf, guarana (*paullinia cupana*) seed, kola nut seed, and galangal root. Materials believed to increase metabolism, prevent fat storage, or burn fat (thermogenic agents or fat reducers) are guggul extract, guarana (*paullinia cupana*) seed, hydroxycitrate, carnitine, acetyl carnitine, cayenne extract, niacin, green tea leaf, wheat bran, lecithin, guggulsterone, salicin or white willow bark, chitosan, lecithin, isomerized safflower glycerides, and *Garcinia cambogia*. Appetite suppressant components include *Hoodia gordonii*, fennel seed, *Griffonia simplicifolia*, pine nut, star anise, *caralluma fimbriata* stem, Korean pine nut (*pinus koraiensis*) seed oil, or L-tyrosine. Fragrant sympathetic nervous system-stimulating compounds, such as fennel oil, grapefruit oil, pepper oil, hyssop oil, sage oil, estragon oil, eucalyptus oil, rosemary oil, cinnamon oil, clove oil, ylang ylang oil, ginger oil, geranium oil, olibanum, limonene, pinene, myrcene or benzyl benzoate, such as described in U.S. Patent Application No. 20030054015 can also be incorporated. Components that aid in relaxation may also be used for their benefit in reducing stress that often leads to overeating; examples of such materials include L-theanine, white willow bark, Korean red panax ginseng root, Siberian ginseng root, linden leaves, or DL-Phenylalanine. Materials that lower blood sugar or triglycerides, such as fenugreek, can also be used. It will be understood that the diet aids can be used in combination, and it may be particularly desired to combine diet aids having different effects or activities, i.e., to combine a thermogenic agent with an appetite suppressant, or a diuretic with a fragrant oil. Exemplary blends of diet aids include a blend of *Hoodia,* guarana seed, fennel seed, anise seed and star anise; a blend of guarana seed, green tea leaf, yerba mate leaf, galangal root, and caffeine; a blend of Korean pine nut (*pinus koraiensis*) seed oil, *caralluma fimbriata* stem and guarana seed; and a blend of white willow bark, panax ginseng, linden leaf, and fenugreek.

The amounts of diet aid added to the composition will differ for each compound or plant material, as it is governed by the known effective dosage for each individual component. The amount will also be determined in connection with the expected frequency of usage of the delivery vehicle. For example, a product that is recommended to be applied once daily (e.g., a lipstick or gloss) will contain a higher concentration of diet aid than one that is expected to be applied repeatedly during the day (a therapeutic lip balm). As a general guideline, the overall concentration of diet aid will be in the range of about 0.001 to about 10% by weight, preferably about 0.01 to about 5%, more preferably about 0.5 to about 3%, and typically, a product will be applied from one to three times daily, e.g., in the morning, at midday, and late afternoon or prior to going out for the evening.

The three component categories described above are the key elements to a lip-based delivery system. However, other components categories can also be added to enhance the aesthetics and/or functionality of the system. For example, it may be desirable to add flavorings to the lip product. Particularly preferred are natural flavorings, essences or flavor-associated fragrances, any which may be added in liquid or powder form: for example fruit flavors, such as strawberry, cherry, orange, lemon, mango, kiwi or banana; herbal flavors, such as mint, lavender, anise or rose; or nut or spice flavors, such as hazelnut, coconut, almond, chocolate, cinnamon, or vanilla (bean); and sugar flavors, such as sugar, sugar vanilla, cookie dough, Oreo® cookie, or sugar cookie. Sweeteners, if used, will preferably be low-calorie or calorie-free, such as saccharine or sucralose, or natural sweeteners, such as stevia or licorice root. However, to adjust the flavoring it may be desirable to add other sweeteners such as sucrose, sorbitol, manitol, lactitol, maltitol, xylitol, erythritol, polydextrose, glucose, isomalt, fructose, lactose, tagatose, aspartame, acesulfame-K, cyclamate, neotame, acesulfame potassium, alitame, or dihydrochalcone. These will typically be added in small quantities, if used at all. Amounts of flavorings employed will depend on the taste effect desired, but will normally be in the range of from about 0.001 to about 3%, by weight of the composition, depending upon the concentration of the flavoring.

If the delivery system is to be used as a lipstick, it may be desirable to add colorants or other components, such as powders, that enhance the appearance of the product on the lips. Colorants used in the delivery system may be any that are acceptable for use in a lip product. These include iron oxides (e.g., red iron oxide, yellow iron oxide or black iron oxide), FD&C certified colors as well as permitted natural colorants. Examples of FD&C certified colors include but are not limited to FD&C Blue #1, FD&C Red 40, FD&C Yellow #5, or FD&C Yellow #6. Examples of natural colorants include caramel color, annatto, turmeric, paprika oleoresin, beta-carotene, carmine, beetroot extract, beet juice, grape skin extract and titanium dioxide. Pearlescent or interference pigments, that can confer a luster to the delivery vehicle may be used if food grade or GRAS. The product may also comprise fillers, such as silica, derivatized cellulose, or starches.

In addition to the diet aid, it may be desirable to add to the vehicle other components, which may provide further advantages to the application of the product. Such components can be referred to generally as "skin benefit agents" for their effect on the lips as well as on the skin. Examples of such skin benefit agents include, but are not limited to, astringents, such as clove oil, menthol, camphor, eucalyptus oil, eugenol, menthyl lactate, witch hazel distillate; antioxidants or free-radical scavengers, such as ascorbic acid, its fatty esters and phosphates, tocopherol and its derivatives, N-acetyl cysteine, sorbic acid and lipoic acid; anti-acne agents, such as salicylic acid and benzoyl peroxide; antimicrobial or antifungal agents such as caprylyl glycol, triclosan, phenoxyethanol, erythromycin, tolnaftate, nystatin or clortrimazole; chelating agents, such as EDTA; anti-aging/anti-wrinkle agents, such as retinoids or hydroxy acids; skin-conditioning agents (e.g., humectants, including miscellaneous and occlusive), antiirritants, such as cola, bisabolol, aloe vera or panthenol, anti-inflammatories, such as acetyl salicylic acid, glycyrrhizic acid or glycyrrhetic acid; humectants, such as alkylene polyols or hyaluronic acid; emollients, such as oily esters or petrolatum; sun protecting agents (organic or inorganic), such as avobenzone, oxybenzone, octylmethoxycinnamate, titanium dioxide or zinc oxide; exfoliating agents (chemical or physical), such as N-acetyl glucosamine, mannose phosphate, hydroxy acids, lactobionic acid, peach kernels, or sea salts; and biologically active peptides, such as palmitoyl pentapeptide or argireline. These supplemental skin benefit agents will be used in the amounts normally known to be effective for that active when used for the intended purpose on the lips.

The lip products of the invention are formulated in the same manner as other cosmetic products of the same type, i.e., lipsticks, lip glosses or lip balms. In most cases, the products of the invention will be anhydrous, as is typical for most products applied to the lips. However, water-containing lip products are also known, and it is possible that the products of the invention also may contain some water, in the form of an emulsion or aqueous dispersion in the oil base. Formulation of lip products of numerous types is well known in the art; examples can be found in *Chemistry and Technology of the Cosmetics and Toiletries Industry,* Williams and Schmitt, eds., Blackie Academic and Professional, Second Edition, 1996 *Harry's Cosmeticology,* Eighth Edition, M. Reiger, ed. (2000), and *Remington: The Science and Practice of Pharmacy,* Twentieth Edition, A. Gennaro, ed., (2003), the contents of each of these being incorporated herein by reference. Examples of additional ingredients appropriate for the inclusion in cosmetic products can be found in *The International Cosmetic Ingredient Dictionary and Handbook,* 10th Edition, 2004, the contents of which are also incorporated herein by reference.

The products of the invention will be applied in the same manner as any corresponding lip product without a diet aid incorporated therein. As an example, a lipstick of the invention will be applied by the user in the morning. Throughout the day, the user will gradually ingest the product of the present invention by virtue of licking or biting the lips, or in the course of consuming food or beverages. As is typical with ordinary lipstick, the user will, at some point in the day, frequently immediately after a meal, or often before going out in the evening, recognize the need for reapplication of the product, and again apply the product of the present invention to the lips. The product of the present invention can be used several times a day, and products can be designed with dosage amounts that correspond to the expected number of reapplications of a product. This may be as few as once, or as many as six or even more times, depending on the type of product and the intended use. For example, a lip balm may be used numerous times throughout the day during the winter, whereas a lipstick may be applied less frequently.

The advantages of the delivery system of the present invention are several. First, it takes advantage of the user's routine daily practices in applying the lip product, and permits the user to desirably achieve a passive intake of a diet aid, thereby not disrupting the daily routine, and possibly leading to a greater level of compliance than may be attainable with the administration of diet aids in traditional form. In addition, the product of the present invention provides an enjoyable means of attempting weight control. Also, in the provision of a product that is largely if not substantially entirely composed of naturally occurring ingredients, it may provide a health benefit not otherwise obtainable with traditional lip products or with traditional forms of diet aids.

The delivery system of the invention is illustrated in the following non-limiting examples.

EXAMPLE 1

This example illustrates a lip gloss according to the present invention.

| Material | Weight percent |
| --- | --- |
| Phase I | |
| Decaglyceryl polyricinoleate | 46.475 |
| Beeswax | 1.950 |
| Hydroxystearic/linoleic/oleic polyglycerides | 4.500 |
| Phase II | |
| Castor seed oil | 46.075 |
| Saccharin/polydecene | 0.200 |
| *Hoodia gordonii* extract | 0.200 |
| Guarana extract | 0.200 |
| Phase III | |
| Cherry fragrance | 0.400 |

Phase I is heated to 85-88° C. while maintaining mixing at 200-375 rpm, being carefully not to aerate. Mixing is continued until all the waxes and butters are melted and the phase is uniform. The active ingredients in Phase II are premixed with propeller, mixing at 350-500 rpm until all actives are dispersed and no particles remain floating or settling. If necessary, Phase II is also premixed with a Silverson mixer to disperse the actives. Phase II premix is slowly added and mixing continued until the batch is uniform, while maintaining the temperature at 85-88° C. Phase III is added to the main mixture and mixed to uniformity. When all the phases are added, the mixture is slowly cooled down using ancor bar propeller to form the lip gloss of the present invention.

EXAMPLE 2

This example illustrates a lipstick according to the invention

| Material | Weight percent |
| --- | --- |
| Phase I | |
| Candelilla wax | 5.500 |
| Beeswax | 8.500 |
| Shea butter | 10.000 |
| Carnauba wax | 2.150 |
| Lecithin | 0.200 |
| CLA Oil 75%* | 0.500 |
| Phase II | |
| Castor seed oil | 32.960 |
| Sodium Saccharin | 0.200 |
| Olive Leaves | 0.100 |
| Wheat Bran Extract | 0.100 |
| Extract of *Ribes Nigrum*** | 0.100 |
| *Griffonia Simplicifolia**** | 0.100 |
| Pinnothin**** | 0.200 |
| Phase III | |
| Organic Sunflower Oil | 21.000 |
| Guarana Seed Extract | 0.200 |
| Phase IV | |
| Vitamin E | 0.500 |
| Phase V | |
| Silica Beads SB-700 | 2.000 |
| Phase VI | |
| BHT | 0.100 |
| Phase VII | |
| Flavor | 1.250 |
| Phase VIII | |
| FD&C Red 40 | 0.035 |
| Organic Sunflower Oil | 0.105 |
| Phase IX | |
| Beetroot Extract | 10.000 |
| Organic Sunflower Oil | 4.000 |
| Lecithin | 0.200 |

*25% linoleic acid, 75% conjugated linoleic acid
**Black currant, Greentech, St. Beauzire, France
***Tournay Biotechnologies, Lamothe Montravel, France
****Pine nut (Korean) extract, Lipid Nutrition North America, Channahon, IL Phases VIII and IX are grinds that are prepared with a roller mill. Phase II is premixed with propeller mixing at 350-500 rpm until all actives have been dispersed and no particulates remain floating or settling. Heat Phase II to 85-88° C. to form premix Phase II. Phase III is premixed with a Silverson if necessary to disperse the guarana. Phase I is heated to 85-88° C. while maintaining mixing at 200-375 r.p.m, being careful not aerate. Mixing is continued until all waxes and butters have melted and the phase is uniform. Premix Phase II is added thereto, and mixing continued until uniform, while maintaining the temperature at 85-88° C. After the combined Phase I and II is uniform, premix phase III is slowly added thereto while maintaining temperature. Phases IV-VII are added thereto sequentially, with mixing after each addition until batch is completely uniform. The premixed Phases VIII and IX are added thereto next, with color matching as necessary. Once all phases are added, the final mixture is poured hot into a mold, and allowed to solidify to form the lipstick of the present invention.

EXAMPLE 3

This example illustrates a lip gloss of the invention.

| Material | Weight percent |
| --- | --- |
| Phase I | |
| Castor seed oil/beeswax/stearic acid/ soy glyceride/carnauba wax* | 50.000 |
| Beeswax | 4.000 |
| Carnauba wax | 1.000 |
| BHT | 0.100 |

-continued

| Material | Weight percent |
|---|---|
| Phase II | |
| Castor seed oil | 10.000 |
| Sodium saccharine | 0.200 |
| *Hoodia gordonii*** | 0.200 |
| Lecithin | 0.200 |
| Wheat bran extract | 0.100 |
| Extract of *Ribes nigrum* | 0.100 |
| *Griffonia simplicifolia* | 0.100 |
| Pine nut extract | 0.100 |
| Phase III | |
| Organic sunflower oil | 16.195 |
| Guarana seed extract | 0.200 |
| Phase IV | |
| CLA 75% | 0.500 |
| Vitamin E | 1.000 |
| Phase V | |
| Flavor | 1.250 |
| Phase VI | |
| FD&C red 40 | 0.350 |
| Organic sunflower oil | 0.105 |
| Phase VII | |
| Beetroot extract | 10.000 |
| Organic sunflower oil | 4.000 |
| Lecithin | 0.200 |

*Strahl & Pitsch, West Babylon, NY
**Stella Labs, Washington Township, NJ

Phases VI and VII are premixed and ground with a ball mill. The active materials in sequence II are premixed with propeller mixing at 350-500 rpm, until all actives are dispersed and no particulates remain floating or settling; the phase is then heated to 85-88° C. If necessary, Phase III is also premixed with a Silverson mixer, to disperse the guarana.

Phase I is heated to 85-88° C. while maintaining mixing at 200-375 rpm, being careful not to aerate. Mixing is continued until all waxes and butters are melted and the phase is uniform. Phase II premix is slowly added and mixing continued until the mixture is uniform, while maintaining the temperature at 85-88° C. Once uniform, Phase III premix is slowly added to the mixture and mixed until uniform, at the same temperature. Phases IV-VII are added sequentially, with mixing after each addition, until the batch is completely uniform. Premixes VI and VII are then added to the main mixture, and mixed to uniformity. Once all phases have been added, the mixture is poured into the desired container and allowed to cool and solidify to form the lip gloss of the present invention.

EXAMPLE 4

This example illustrates a lip gloss of the invention.

| Material | Weight percent |
|---|---|
| Phase I | |
| Castor seed oil/beeswax/stearic acid/soy glyceride/carnauba wax* | 50.000 |
| Decaglyceryl polyricinoleate | 14.000 |
| Candelilla wax | 2.000 |

-continued

| Material | Weight percent |
|---|---|
| BHT | 0.100 |
| Castor seed oil | 14.000 |
| Sodium saccharine | 0.200 |
| Pine nut (Korean) extract | 0.100 |
| Phase II | |
| Extract of *Ribes nigrum* | 0.100 |
| Glycerin | 5.000 |
| *Caralluma fimbriata* stem extract | 1.000 |
| Guarana seed extract | 0.200 |
| Decaglyceryl polyricinoleate | 3.000 |
| Maltodextrin | 1.000 |
| Phase III | |
| Titanium dioxide | 1.000 |
| Iron oxide (yellow) | 0.185 |
| Black Iron oxide | 0.105 |
| Castor seed oil | 2.800 |
| Phase IV | |
| Isomerized safflower glycerides | 0.500 |
| Vitamin E | 1.000 |
| Phase V | |
| Castor seed oil | 2.000 |
| Flavor | 1.710 |

*Strahl & Pitsch, West Babylon, NY

Phase I ingredients are combined and heated to 80-85° C. with prop mixing until uniform forming the Phase I mixture. Phase II ingredients are premixed with prop mixing until ingredients are solubilized, and are heated to 85° C. forming the Phase II premixture. Phase III ingredients are added to the Phase I mixture and homogenized to form the Phase III mixture. The Phase II premixture is added to the Phase III mixture to form the Phase II/III mixture. The ingredients of Phase IV are added to the Phase II/III mixture and are mixed for 15 minutes while avoiding splashing and while being aerated to form the Phase IV mixture. Cool the Phase IV mixture to 40-45° C. and then add Phase V ingredients. Mix the Phase IV mixture and Phase V ingredients for 10 minutes to form the final mixture. The final mixture is cooled to room temperature forming the lip gloss of the present invention.

EXAMPLE 5

This example illustrates a lipstick according to the invention

| Material | Weight percent |
|---|---|
| Phase I | |
| Candelilla wax | 10.000 |
| Beeswax | 3.000 |
| Shea butter | 7.000 |
| Carnauba wax | 2.550 |
| Lecithin | 0.200 |
| BHT | 0.100 |
| Castor seed oil | 42.000 |
| Sodium Saccharin | 0.200 |
| Pine nut (Korean) seed oil | 0.200 |
| Sunflower seed Oil | 15.000 |
| Vitamin E | 1.000 |
| Isomerized linoleic acid/linoleic acid | 0.500 |
| Phase II | |
| *Caralluma fimbriata* stem extract | 1.000 |
| *Ribes Nigrum*** | 0.100 |

-continued

| Material | Weight percent |
|---|---|
| Glycerin | 2.500 |
| Decaglyceryl polyricinoleate | 1.000 |
| Maltodextrin | 1.000 |
| Guarana Seed extract | 0.200 |
| Phase III | |
| Titanium dioxide | 1.000 |
| Red iron oxide | 0.105 |
| Iron oxide (Yellow) | 0.180 |
| Castor seed oil | 1.000 |
| Phase IV | |
| Silica Beads SB-700 | 2.000 |
| Phase V | |
| Flavor | 1.250 |
| Castor Seed Oil | 4.000 |

**Black currant, Greentech, St. Beauzire, France

Phase I ingredients are combined and heated to 80-85° C. with prop mixing until uniform forming the Phase I mixture. Phase II ingredients are premixed with prop mixing until ingredients are solubilized, and are heated to 85° C. forming the Phase II premixture. Phase III ingredients are added to the Phase I mixture and homogenized to form the Phase III mixture. The Phase II premixture is added to the Phase III mixture to form the Phase II/III mixture. The ingredients of Phase IV are added to the Phase II/III mixture and are mixed for 15 minutes while avoiding splashing and while being aerated to form the Phase IV mixture. Add Phase V ingredients to the Phase IV mixture and mix for 10 minutes to form the final mixture. The final mixture is formed into the lipstick of the present invention.

What we claim is:

1. A lipstick composition comprising at least one naturally occurring oil, at least one naturally occurring wax, and at least one naturally occurring diet aid component comprising at least one of pine nut (Korean) seed oil, *caralluma fimbriata* stem extract, and guarana seed extract.

2. A lip gloss composition comprising at least one naturally occurring oil, at least one naturally occurring wax, and at least one naturally occurring diet aid component comprising at least one of pine nut (Korean) seed oil, *caralluma fimbriata* stem extract, and guarana seed extract.

3. The composition of claim 1 wherein the diet aid is a combination of a lecithin, a pine nut (Korean) seed oil, a *caralluma fimbriata* stem extract, an extract of ribes nigrum, guarana seed extract and isomerized safflower glycerides.

* * * * *